(12) United States Patent
Xu et al.

(10) Patent No.: US 11,662,107 B2
(45) Date of Patent: May 30, 2023

(54) ISOLATING CONSULTING TABLE

(71) Applicant: SHANDONG SADY MEDICAL TECHNOLOGY CO. LTD., Tai'an (CN)

(72) Inventors: Xiaoshuai Xu, Tai'an (CN); Ping Wang, Tai'an (CN); Qidi Xu, Tai'an (CN); Gang Hao, Tai'an (CN); Lepeng Li, Tai'an (CN); Zhaoshui Zhang, Tai'an (CN)

(73) Assignee: SHANDONG SADY MEDICAL TECHNOLOGY CO. LTD., Tai'an (CN)

( * ) Notice: Subject to any disclaimer, the term of this patent is extended or adjusted under 35 U.S.C. 154(b) by 212 days.

(21) Appl. No.: 17/139,418

(22) Filed: Dec. 31, 2020

(65) Prior Publication Data
US 2022/0026084 A1 Jan. 27, 2022

(30) Foreign Application Priority Data

Jul. 27, 2020 (CN) .......................... 202010740794.0

(51) Int. Cl.
*A47B 97/00* (2006.01)
*A61L 2/02* (2006.01)
*F24F 8/30* (2021.01)
*A61L 9/22* (2006.01)
(Continued)

(52) U.S. Cl.
CPC ............ *F24F 5/0096* (2013.01); *A47B 21/00* (2013.01); *A47B 97/00* (2013.01); *A61L 9/22* (2013.01); *F24F 8/30* (2021.01); *A61L 2209/16* (2013.01)

(58) Field of Classification Search
CPC ......... A47B 97/00; A47B 21/00; A61L 2/022; A61L 9/22; F24F 8/30
See application file for complete search history.

(56) References Cited

U.S. PATENT DOCUMENTS

2022/0125199 A1* 4/2022 Pike .......................... F24F 7/06

FOREIGN PATENT DOCUMENTS

| CN | 208017713 U | 10/2018 |
| CN | 108837172 A | * 11/2018 |

OTHER PUBLICATIONS

English Translation of International Document No. CN 108837172 A provided by espacenet.com: Xiaoshuai Xu; Isolation Type Disinfection Diagnosis and Treatment Table Equipment and Use Method Thereof; Nov. 20, 2018 (Year: 2018).*

* cited by examiner

*Primary Examiner* — Kevin Joyner
(74) *Attorney, Agent, or Firm* — Muncy, Geissler, Olds & Lowe, P.C.

(57) ABSTRACT

The present invention relates to a novel isolating consulting table. The novel isolating consulting table includes a table body and an air outlet pipe, wherein an air inlet duct is inlaid on the table top; the air inlet duct and the air outlet pipe are located in the same vertical plane; an electric ion purification and disinfection system is arranged in the air inlet duct; the table body is provided with a pneumatic device; an air inlet and an air outlet of the pneumatic device are communicated with an air outlet of the air inlet duct and an air inlet duct of the air outlet pipe, respectively; the air outlet pipe includes a ventilation pipe, and an air outlet guide hood located at an air outlet of the ventilation pipe; an air outlet side of the air outlet guide hood is arranged toward the air inlet duct.

5 Claims, 6 Drawing Sheets

(51) Int. Cl.
*A47B 21/00* (2006.01)
*F24F 5/00* (2006.01)

ISOLATING CONSULTING TABLE

TECHNICAL FIELD

The present invention relates to the technical field of consulting tables, in particular to a novel isolating consulting table.

BACKGROUND

A consulting table is a table where a doctor performs basic diagnosis (referring to looking, listening, questioning and feeling the pulse). However, for consulting tables in infectious diseases departments and ordinary consulting rooms in hospitals, generally, a doctor wears a mask to perform basic diagnosis at one side of the consulting table while a patient sits on the other side of the table, leaving the doctor highly susceptible to infectious diseases. With the development of the times, the consulting table in the infectious diseases departments usually uses glass for separation, but such a consulting table adversely affects the interaction between the doctor and the patient. Some consulting tables may adopt ultraviolet rays for sterilization, which usually causes exposure of the ultraviolet rays. Ordinary tables basically without any protective measures serve as the consulting tables in ordinary consulting rooms, lacking safeguard for the lives of medical workers.

In the prior art, a granted utility model patent with the publication number of CN208017713U discloses an examination table for infectious diseases, including an examination table body. A bracket and a lamp box are arranged on the examination table body. Three support legs and a disinfection device are arranged at the bottom end of the examination table body. A reading clip is arranged on the lamp box in which an LED lamp is arranged. An air filter, an ultraviolet disinfection lamp and a centrifugal fan are sequentially arranged in the disinfection device from top to bottom. A fixing sleeve and a baffle are arranged on the bracket. A garbage can is arranged on the fixing sleeve. In the utility model, the structure design is reasonable, the use is easy, a doctor can check a chest radiograph data at any time conveniently, and health of a medical worker is ensured as a patient with an infectious disease is prevented from infecting the doctor when he/she examines the infectious patient.

However, the above existing technical solution has a defect of a high probability of ultraviolet light leakage, which adversely affects the health of doctors and patients.

SUMMARY

An object of the present invention is to provide a novel isolating consulting table. The novel isolating consulting table can not only purify and disinfect a visiting environment, but also form an effective wind screen between a doctor and a patient, such that the infection of a medical worker and cross infection between the doctor and the patient are avoided, thereby ensuring the life safety of the doctor.

The object of the present invention is achieved by the following technical solutions.

A novel isolating consulting table includes a table body and an air outlet pipe vertically arranged on the table body, wherein an air inlet duct is inlaid on the table top of the table body; the air inlet duct and the air outlet pipe are located in the same vertical plane; an electric ion purification and disinfection system is arranged in the air inlet duct; the table body is provided with a pneumatic device; an air inlet and an air outlet of the pneumatic device are communicated with an air outlet of the air inlet duct and an air inlet duct of the air outlet pipe, respectively; the air outlet pipe includes a ventilation pipe, and an air outlet guide hood located at an air outlet of the ventilation pipe; an air outlet side of the air outlet guide hood is arranged toward the air inlet duct; and an electric control unit and a switch control panel can switch on/off and electrically control the pneumatic device and the electric ion purification and disinfection system.

Preferably, a strip-shaped notch is formed in the table top of the table body, and is inlaid with the air inlet duct consisting of a cover plate for preliminary filtering and a ventilation slot; the electric ion purification and disinfection system is clamped in the ventilation slot, and is formed by a plurality of electric ion purification and disinfection modules connected in parallel; and a conductive electrode is arranged on each of the electric ion purification and disinfection modules.

Preferably, the electric ion purification and disinfection modules are sequentially connected in parallel, and a space is reserved at an air inlet of the ventilation slot after the electric ion purification and disinfection modules are clamped in the ventilation slot.

Preferably, the pneumatic device is mounted below the table body; an air outlet of the pneumatic device is located right under the air outlet pipe; and the pneumatic device includes a fan and an air guide hood located outside the fan.

Preferably, the electric control unit is located right under the pneumatic device; and the switch control panel is located on the surface of the table top.

Preferably, bosses fitting the space reserved in the ventilation slot are arranged at both ends of the primary filter cover plate.

In summary, the present invention has the following beneficial effects.

In the present invention, after external air sucked into the electric ion filtration and disinfection system through the pneumatic device is filtered, purified and disinfected, new air is blown out from the air outlet pipe by the pneumatic device, such that air circulation is realized. Meanwhile, the air flow forms a wind screen between the air inlet and the air outlet to block a passage of germs brought out by the patient's breathing or speaking flowing to a medical worker. Under the flowing action of the wind screen, air carrying the germs is introduced into the electric ion filtration and disinfection system, such that the visiting environment is purified, thereby avoiding the infection of the medical worker and cross infection between patients.

The reference numerals in the figures: 1, table body; 2, air outlet pipe; 21, ventilation pipe; 22, air outlet guide hood; 3, air inlet duct; 31, cover plate for preliminary filtering; 311, boss; 32, electric ion purification and disinfection system; 321, electric ion purification and disinfection module; 3211, electrode; 33, ventilation slot; 4, pneumatic device; 41, fan; 42, air guide hood; 5, electric control unit; and 6, switch control panel.

DETAILED DESCRIPTION

In order to facilitate the understanding of those skilled in the art, the present invention will be further described below with reference to the embodiments and the accompanying drawings, and the content mentioned in the embodiments does not limit the present invention. The present invention will be described in detail below with reference to the accompanying drawings.

The present invention will be further described in detail below with reference to the accompanying drawings.

Figure 1:
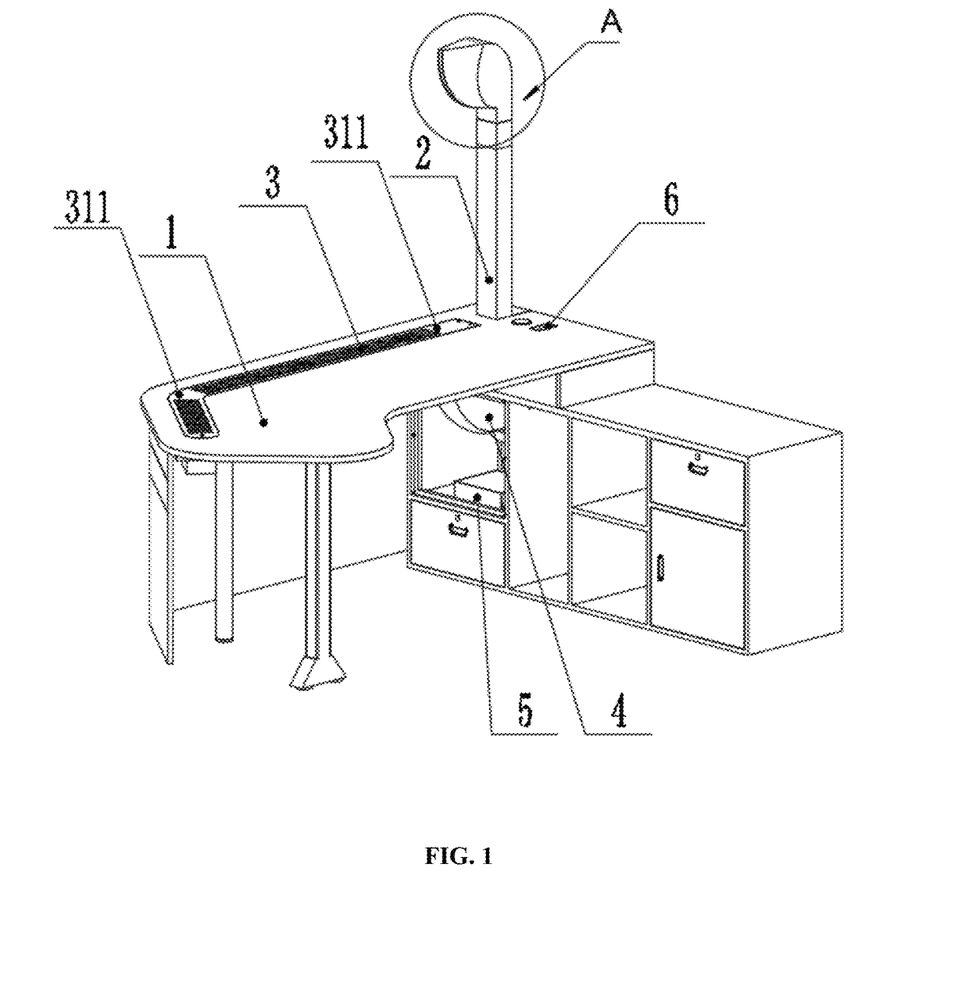
FIG. 1 is a schematic diagram of an overall structure of the present invention.
Figure 2:
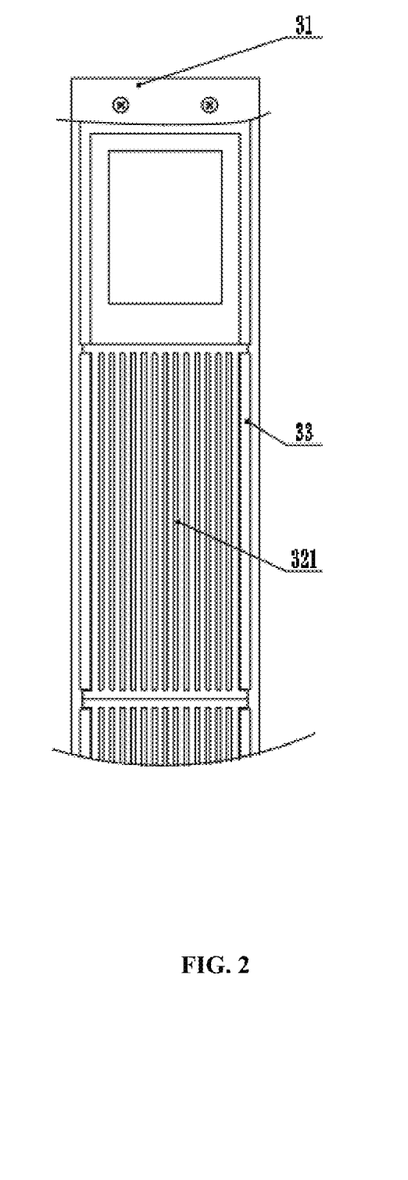
FIG. 2 is a schematic diagram of a partial structure of an air inlet pipe in FIG. 1 without a cover plate for preliminary filtering.

Referring to FIGS. 1 and 2, a novel isolating consulting table includes a table body 1 and an air outlet pipe 2 vertically arranged on the table body 1. An air inlet duct 3 is inlaid on the table top of the table body 1. The air inlet duct 3 and the air outlet pipe 2 are located in the same vertical plane. An electric ion purification and disinfection system 32 is arranged in the air inlet duct 3. The table body 1 is provided with a pneumatic device 4. An air inlet and an air outlet of the pneumatic device 4 are communicated with an air outlet of the air inlet duct 3 and an air inlet duct of the air outlet pipe 2, respectively. The air outlet pipe 2 includes a ventilation pipe 21, and an air outlet guide hood 22 located at an air outlet of the ventilation pipe 21. An air outlet side of the air outlet guide hood 22 is arranged toward the air inlet duct 3. An electric control unit 5 and a switch control panel 6 can switch on/off and electrically control the pneumatic device 4 and the electric ion purification and disinfection system 32.

In the present invention, after external air sucked into the electric ion purification and disinfection system 32 through the pneumatic device 4 from the cover plate for preliminary filtering 31 on the air inlet duct 3 is filtered, purified and disinfected, new air is blown out from the air outlet guide hood 22 on the air outlet pipe 2 by the pneumatic device 4, such that air circulation is realized. Meanwhile, the air flow forms a wind screen between the air inlet duct 3 and the air outlet guide hood 22 to block a passage of germs brought out by the patient's breathing or speaking flowing to a medical worker. Under the flowing action of the wind screen, air carrying the germs is introduced into the electric ion purification and disinfection system, such that a visiting environment is purified, thereby avoiding the infection of the medical worker and cross infection between patients.

Figure 3:
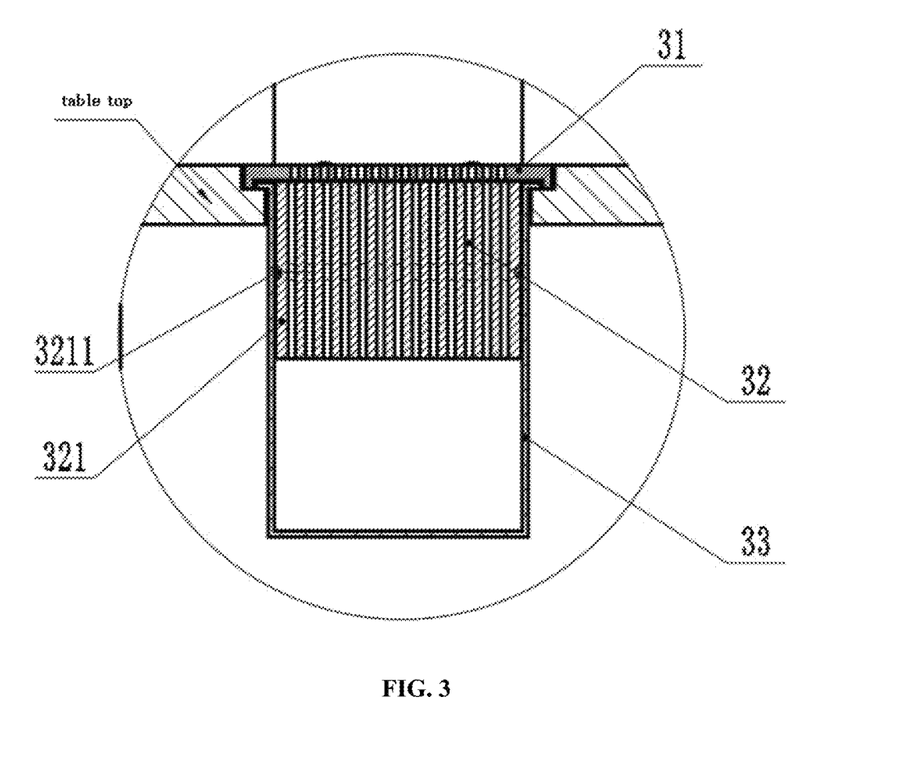
FIG. 3 is a schematic longitudinal section view of the air inlet pipe in FIG. 1.
Figure 4:
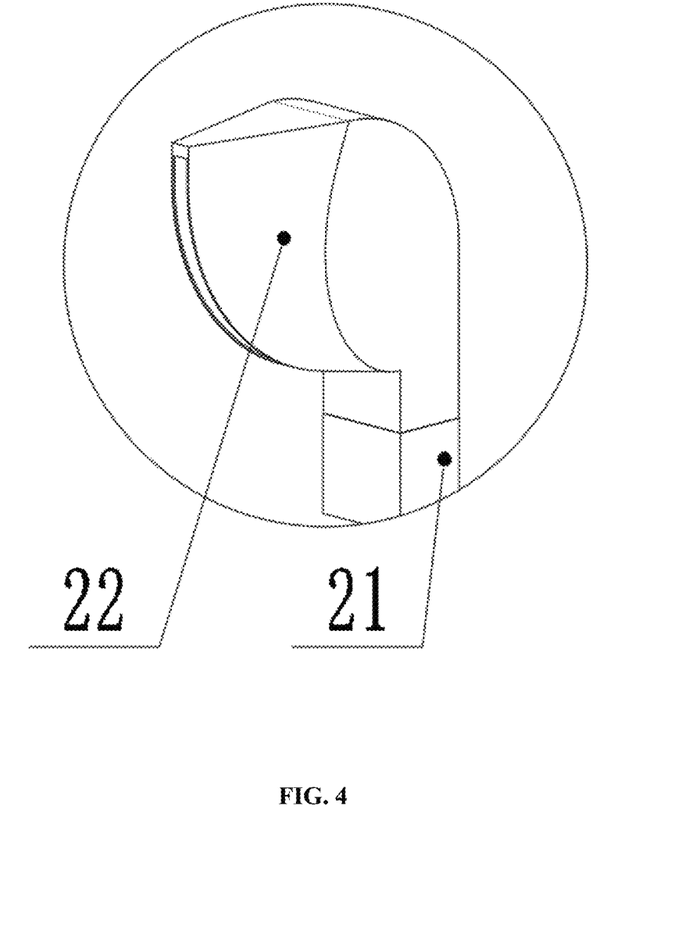
FIG. 4 is a schematic structure diagram of a portion A in FIG. 1.

Referring to FIGS. 3 and 4, a strip-shaped notch is formed in the table top of the table body 1, and is inlaid with the air inlet duct 3 consisting of a cover plate for preliminary filtering 31 and a ventilation slot 33. The electric ion purification and disinfection system 32 is tightly clamped in the ventilation slot, and is formed by a plurality of electric ion purification and disinfection modules 321 connected in parallel. A conductive electrode 3211 is arranged on each of the electric ion purification and disinfection modules 3211.

After power on, the electric ion purification and disinfection modules 321 purify and disinfect air circulating therein. The arranged cover plate for preliminary filtering 31 can prevent large particles or objects from entering the electric ion purification and disinfection modules 321.

The electric ion purification and disinfection modules 321 are sequentially connected in parallel. The reason for the parallel connection is to facilitate maintenance. A space is reserved at an air inlet of the ventilation slot 33 after the electric ion purification and disinfection modules 321 are clamped in the ventilation slot 33. This arrangement facilitates the taking and placing of the electric ion purification and disinfection modules 321.

Figure 5:
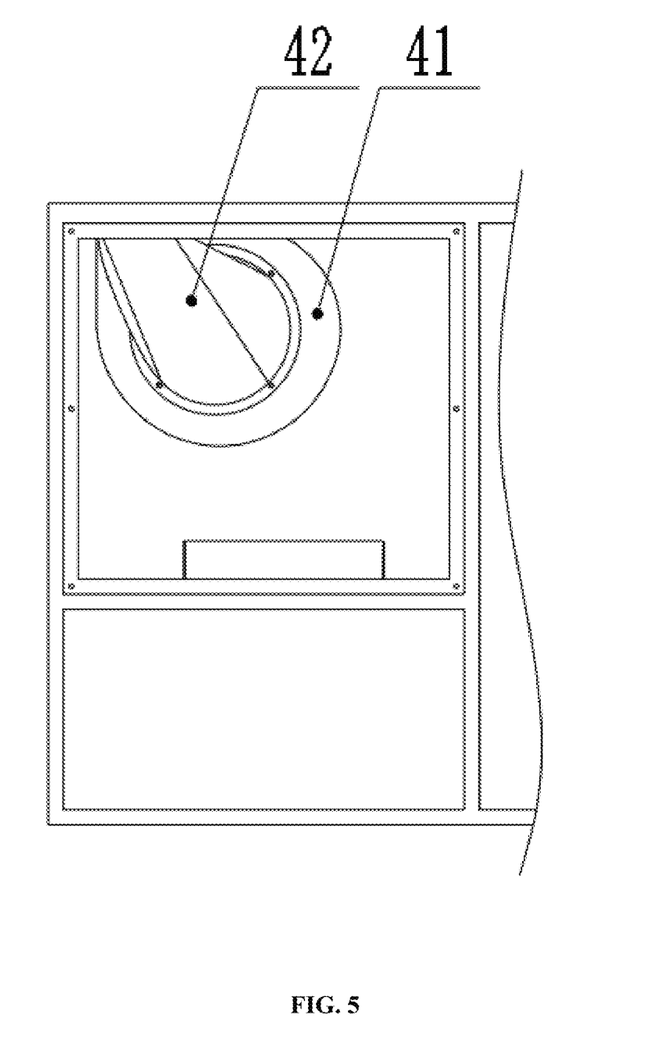
FIG. 5 is a schematic structure diagram of a pneumatic device in FIG. 1.

The pneumatic device 4 is mounted below the table body 1. An air outlet of the pneumatic device 4 is located right under the air outlet pipe 2. The pneumatic device 4 includes a fan 41 and an air guide hood 42 located outside the fan 41.

Since the air direction at the air inlet and the air direction at the air outlet of the pneumatic device 4 are vertical, a specially made air guide hood 42 is required for guiding. The air guide hood 42 plays a role of sealing and guiding the purified and disinfected air to prevent secondary pollution of the purified air.

Referring to FIG. 5, the electric control unit 5 is located right under the pneumatic device 4; and the switch control panel 6 is located on the surface of the table top. With this arrangement, it is convenient for the medical worker to start and close the pneumatic device.

Bosses 311 fitting the space reserved in the ventilation slot 33 are arranged at both ends of the primary filter cover plate 31. This arrangement can avoid insufficient disinfection and sterilization of the whole ventilation slot 33 caused by a failure of the disinfection and sterilization of the space reserved in the ventilation slot 33.

Each of the two side surfaces of the electric ion purification and disinfection module 321 has a slope. After the electric ion purification and disinfection module 321 is clamped into the ventilation slot, the inclined side surfaces can be attached to the inner wall of the ventilation slot 33, thereby improving the air purification efficiency.

Figure 6:
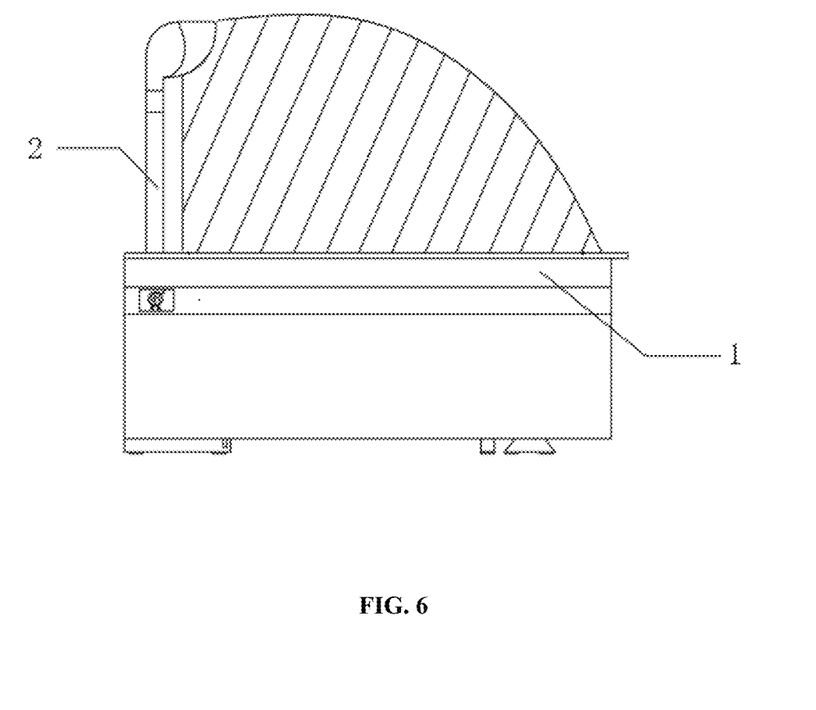
FIG. 6 is a schematic diagram of forming a wind screen.

The working process is as follows. Referring to FIG. 6, the electric control unit 5 controls the pneumatic device 4; the electric ion purification and disinfection modules 321 start; the air enters the electric ion purification and disinfection modules 321 from the cover plate for preliminary filtering at the air inlet to be filtered, purified and disinfected; and the air after purification and disinfection enters the fan and is discharged from the air outlet pipe. A wind screen is formed between the air outlet and the air inlet. Under the flowing action of the wind screen, air carrying the germs is filtrated and disinfected, such that the visiting environment is purified, thereby avoiding the infection of the medical worker and the cross infection between patients.

The foregoing is only the preferred embodiments of the present invention and does not limit the present invention in any form. Although the present invention has been disclosed in the preferred embodiments as above, the preferred embodiments are not intended to limit the present invention. Any person skilled in the art can make some changes or modifications as equivalent embodiments with equivalent changes without departing from the scope of the technical solution of the present invention by using the technical content disclosed above. Any simple modifications, equivalent changes and modifications made to the above embodiments according to the technology of the present invention without departing from the content of the technical solution of the present invention should be included within the scope of the technical solution of the present invention.

What is claimed is:

1. A novel isolating consulting table, comprising:
   a table body; and
   an air outlet pipe vertically arranged on the table body, wherein an air inlet duct is inlaid on a table top of the table body; the air inlet duct and the air outlet pipe are located in a same vertical plane; an electric ion purification and disinfection system is arranged in the air inlet duct; the table body is provided with a pneumatic device; an air inlet and an air outlet of the pneumatic device are communicated with an air outlet of the air inlet duct and an air inlet duct of the air outlet pipe, respectively; the air outlet pipe comprises a ventilation pipe, and an air outlet guide hood located at an air outlet of the ventilation pipe; an air outlet side of the air outlet guide hood is arranged toward the air inlet duct; and an electric control unit and a switch control panel can switch on/off and electrically control the pneumatic device and the electric ion purification and disinfection system, wherein a strip-shaped notch is formed in the table top of the table body, and is inlaid with the air inlet duct consisting of a cover plate for preliminary filtering and a ventilation slot; the electric ion purification and disinfection system is clamped in the ventilation slot, and is formed by a plurality of electric ion purification and disinfection modules connected in parallel; and a conductive electrode is arranged on each of the electric ion purification and disinfection modules.

2. The novel isolating consulting table according to claim 1, wherein the electric ion purification and disinfection modules are sequentially connected in parallel, and a space is reserved at an air inlet of the ventilation slot after the electric ion purification and disinfection modules are clamped in the ventilation slot.

3. The novel isolating consulting table according to claim 2, wherein the pneumatic device is mounted below the table body; the air outlet of the pneumatic device is located right under the air outlet pipe; and the pneumatic device comprises a fan and an air guide hood located outside the fan.

4. The novel isolating consulting table according to claim 3, wherein the electric control unit is located right under the pneumatic device; and the switch control panel is located on a surface of the table top.

5. The novel isolating consulting table according to claim 4, wherein bosses fitting the space reserved in the ventilation slot are arranged at both ends of the cover plate.

\* \* \* \* \*